United States Patent
Macey

(10) Patent No.: US 6,193,725 B1
(45) Date of Patent: Feb. 27, 2001

(54) METHOD AND APPARATUS FOR REMOVING A ROD FROM TISSUE OF AN ORGANISM

(76) Inventor: Theodore I. Macey, 1212 Twin Bay Dr., Ft. Walton Beach, FL (US) 32547

( * ) Notice: Subject to any disclaimer, the term of this patent is extended or adjusted under 35 U.S.C. 154(b) by 0 days.

(21) Appl. No.: 09/485,490
(22) PCT Filed: Jun. 11, 1999
(86) PCT No.: PCT/US99/13231
  § 371 Date: Feb. 11, 2000
  § 102(e) Date: Feb. 11, 2000
(87) PCT Pub. No.: WO99/63898
  PCT Pub. Date: Dec. 16, 1999

Related U.S. Application Data

(60) Provisional application No. 60/089,051, filed on Jun. 12, 1998.

(51) Int. Cl.⁷ ........................................ A61F 5/04
(52) U.S. Cl. ................ 606/104; 606/62; 606/99
(58) Field of Search .................. 606/62, 63, 67, 606/72, 99, 104, 86

(56) References Cited

U.S. PATENT DOCUMENTS

| | | | |
|---|---|---|---|
| 3,626,935 | * | 12/1971 | Pollock et al. . |
| 4,399,813 | * | 8/1983 | Barber . |
| 4,423,721 | * | 1/1984 | Otte et al. . |
| 5,766,180 | * | 6/1998 | Winquist ............................. 606/104 |

* cited by examiner

Primary Examiner—Michael Buiz
Assistant Examiner—David O. Reip
(74) Attorney, Agent, or Firm—Andrew F. Reish

(57) ABSTRACT

A universal rod adapter for removing a rod from tissue of an organism includes a link with at least one bore and a first mating device. The adapter further includes a device for engaging a wall of an aperture of the rod. The rod adapter employs an expanding device which expands the engaging device so that the engaging device facilitates the removal of the rod from the tissue of the organism by providing a substantially non-slip gripping mechanism which attaches to the wall of the aperture of the rod.

23 Claims, 2 Drawing Sheets

METHOD AND APPARATUS FOR REMOVING A ROD FROM TISSUE OF AN ORGANISM

This application is a 371 of PCT/US99/13231, filed Jun. 11, 1999, which claims benefit of 60/089,051, filed Jun. 12, 1998.

BACKGROUND OF THE INVENTION

1. Field of the Invention

The present invention relates to a method and apparatus for removing a rod from the tissue of an organism. The method and apparatus employ a link, a fastener, a hollow sleeve and an expanding device which form a universal adapter for removing rods from tissue such as bone. The universal adapter is capable of removing many different size rods having various diameters.

2. Description of the Background Art

Various types of rods are used in surgery to repair fractures of: human tissue, such as the fracture of bones. Rods typically provide a solid and secure mechanism for joining broken bones so that the bones will heal in a substantially controlled and properly oriented manner. Various rod removal and insertion devices exist in the conventional art for the removal and insertion of rods into bones. Many of the rod insertion and removal devices include threaded ends with a predetermined diameter which match with a specific rod having the identical diameter and threading as the insertion and/or removal device. For example, in U.S. Pat. No. 2,638,092 (Dorr), an intramedullary nail inserted into a bone includes a threaded end which engages a removal/insertion device having a threaded socket where both the threaded end and the threaded socket have corresponding diameters and threads which are designed specifically for each other. In orthopedic surgery, it has become commonplace to insert rods of varying diameters for different types of bone fractures. Furthermore, manufacturers of such rods require specific individual tools for each rod. In other words, each type of rod requires a specific tool for the insertion and/or removal of the rod with respect to the living tissue. Such a design substantially inflates the cost of both the rods and the insertion/removal tools, while also creating a potential hazard during emergency removal of the rods.

In an emergency situation where speedy removal of the rods from the tissue is required, the conventional art requires the matching of the rod with a respective removal tool. Locating the appropriate removal tool for a respective rod often requires an inordinate amount of time for the medical practitioner to perform such a task. Often, rods of the conventional art would require identifying serial numbers and/or part numbers to facilitate the identification of the appropriate removal tool. Such a system requires that a medical practitioner identify the serial number and/or part number of the rod and to match the serial number and/or part number of the rod with a published listing in order to identify the appropriate removal tool number. Such a matching process also requires an inordinate amount of time of the medical practitioner, especially during an emergency situation.

Accordingly, a need in the art exists for a method and apparatus for removing a rod from tissue of an organism without requiring an array of removal tools which are designed for rods having different diameters and/or threading patterns. A further need exists in the art for a method and apparatus for removing a rod from tissue of an organism which forms a universal adapter which can remove any type of rod that has a diameter and/or threading pattern which is within the range of diameters contemplated by the design of the universal adapter. A further need exists in the art for the removal of a rod from the tissue of an organism in a substantially efficient manner during an emergency situation.

SUMMARY OF THE INVENTION

Accordingly, it is a primary object of the present invention to provide a method and apparatus for removing a rod from tissue of an organism which can engage and remove any type of rod having a diameter and/or threading pattern which is within the range of diameters contemplated by the universal rod adapter. It is a further object of the present invention to provide a method and apparatus which facilitates the removal of a rod from the tissue of an organism by providing a substantially non-slip gripping mechanism which attaches to a rod wall surrounding an aperture.

Another object of the present invention is to provide a method and apparatus for the rapid removal of a rod from tissue of an organism to avoid the inordinate delay of existing systems which require one to match serial numbers and/or part numbers of a corresponding rod to a particular removal tool.

A further object of the present invention is to provide a method and apparatus for removing a rod from the tissue of an organism which employs a universal rod extractor which can remove at least one of femoral and tibial rods.

An additional object of the present invention is to provide a method and apparatus for removing a rod from tissue which employs a universal adapter which will fit an array of rods of differently sized internal diameters.

Another object of the present invention is to provide a method and apparatus from removing a rod from tissue which substantially reduces the costs associated with the removal of rods from living tissue.

It is a further object of the present invention to provide a method and apparatus for removing a rod from tissue of an organism which substantially reduces the time, effort, and resources expended by the medical practitioner, especially by eliminating the task of matching rod serial number and/or part numbers with an appropriate removal tool.

Another object of the present invention is to provide a method and apparatus for removing a rod from the tissue of an organism which employs a relatively simple structure that substantially increases manufacturing efficiency thereof.

A further object of the present invention is to provide a method and apparatus for removing a rod from tissue which employs a link that forms part of a substantially non-slip gripping mechanism which attaches to a rod wall surrounding an aperture therein while also providing an attachment surface for a slap hammer/rod mechanism used to vibrate the link in addition to a fastener, a hollow sleeve, and an expanding device.

Another object of the present invention is to provide a method and apparatus for removing a rod from tissue which will facilitate axial movement of the rod.

A further object of the present invention is to provide a method and apparatus for removing a rod from tissue of an organism which will substantially reduce the potential for damage to the tissue such as lacerations, bone chipping, cracking or splitting during the removal of the rod from the tissue.

As a further object of the present invention to provide a method and apparatus for removing a rod from tissue of an organism which provides a link which includes structures which are designed to mate with respective mating structures of an expandable engaging device. The respective mating structures of the link and the engaging device are substantially designed to prevent any rotation of the engaging device relative to the link.

It is a further object of the present invention to provide a method and apparatus for removing a rod from tissue of an organism which employs a universal rod adapter which is designed to remove femoral and tibial rods, and more specifically intramedullary femoral or tibial rods.

These and other objects of the present invention are fulfilled by providing a universal rod adapter for removing a rod from tissue of an organism, where the rod adapter comprising a link with at least one bore and first means for mating; means for engaging a wall surrounding an aperture of the rod, the aperture having a diameter, the engaging means including a hollow sleeve with a first diameter having a plurality of openings and frictional members disposed between the openings. The engaging means further including a second means for mating disposed on one end of the sleeve; means for expanding the engaging means, the expanding means including an outer angled surface, the expanding means further including an internal threaded bore and projections on the outer angled surface; and a fastener having threads, the fastener engaging with the expanding means and moving the expanding means within the engaging means, a projection of the expanding means being disposed in a respective opening of the engaging means during movement of the expanding means, the first mating means being engaged with the second mating means and substantially preventing rotational movement of the expanding means relative to the link, the expanding means changes the first diameter of the engaging means to a second diameter which is substantially greater than the first diameter and substantially equal to the diameter of the aperture in order to provide frictional engagement between the frictional members and the wall of the aperture, whereby the engaging means facilitates the removal of the rod from the tissue of the organism by providing a substantially non-slip gripping mechanism which attaches to the wall of the aperture of the rod.

In addition, these and other objects of the present invention are also accomplished by providing a method for removing a rod from tissue of an organism comprising the steps of providing the link with at least one bore and a first mating structure; providing an expanding device with an outer angled surface, the expanding device further including an internal threaded bore and projections on the outer surface; providing a hollow sleeve with a plurality of openings and frictional members disposed between the openings, the hollow sleeve further including a second mating structure on one end of the sleeves; providing a fastener having threads; placing the expanding device in an aperture of the rod; placing the sleeve within the aperture of the rod; sliding the sleeve over the engaging device; coupling the first mating structure with the second mating structure; placing the threaded fastener into the at least one bore; threadily engaging the fastener with the expanding device; rotating the fastener in a defined direction so the expanding device moves into the sleeve hollow of the while expanding the frictional members to press against the surrounding wall of the aperture of the rod; and pulling the link in a direction to remove the rod from the tissue of the organism.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

Figure 1:
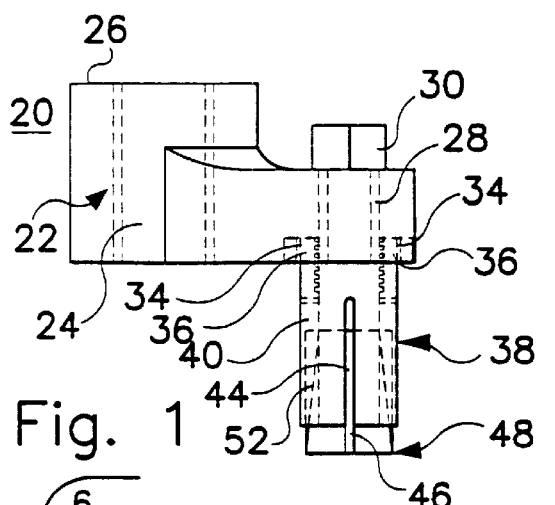
FIG. 1 is a side view of a first embodiment of the universal rod adapter of the present invention.

Referring in detail to the Drawings and with particular reference to FIG. 1, a universal rod adapter 20 is shown. It is contemplated that the universal rod adapter 20 will be used to remove intramedullary femoral or tibial rods within the femur and tibia bones of the human body. However, other types of tissues and other organisms are not beyond the scope of the present invention. For example, the universal rod adapter can be used to remove rods disposed in other parts of the human body where such rods are used to secure and join broken parts of tissue. Other types of organisms include, but are not limited to, animals and plants.

Figure 4:
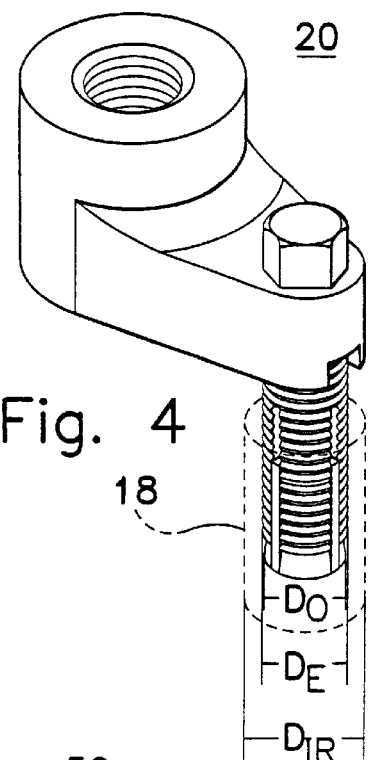
FIG. 4 is a perspective view of the first embodiment of the universal adapter in a fully assembled state.
Figure 2:
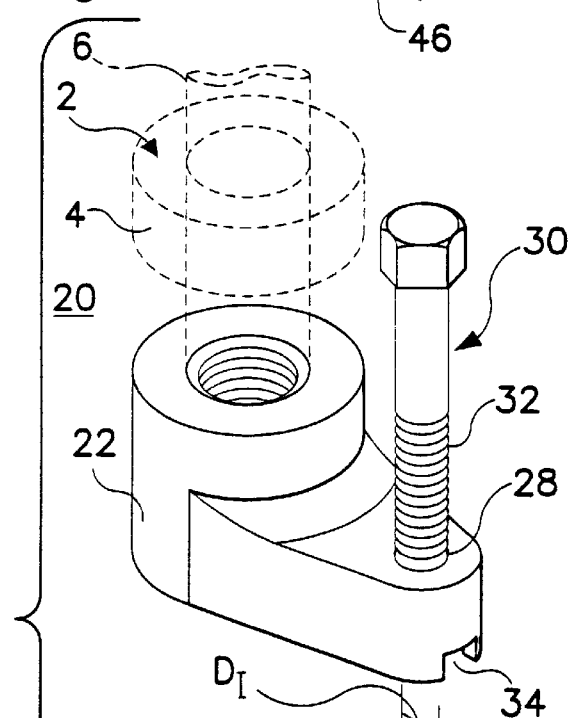
FIG. 2 is a perspective view of the first embodiment of the universal rod adapter of the present invention in a partially disassembled state.

As seen in FIGS. 1, 2 and 4, the universal rod adapter includes link 22 which has an oblong shape. Within the link 22 is a threaded bore 24 which provides support for a slap hammer/rod mechanism 2. The slap hammer 4 of the slap hammer/rod mechanism 2 is designed to impact the substantially planar surface 26 surrounding the threaded bore 24 into which rod 6 is mated. While the threaded bore 24 provides a fastening mechanism for the rod 6 of the slap hammer/rod mechanism 2, other types of fastening mechanisms are not beyond the scope of the present invention. Other types of fastening mechanisms for attaching to a slap hammer/rod mechanism include, but are not limited to, adhesives, frictional engaging surfaces such as slots or projections, or other surfaces which receive fastening structures such as ball and socket joints, bearing structures, or any mechanical devices which promote fastening between two mechanical structures. While the link 22 is preferably made out of stainless or surgical grade steel, other materials may be employed from other metals and/or metal alloys (metal mixtures). Other materials include, but are not limited to, aluminum, carbon, cobalt, chromium, iron, nickel, tin, titanium and zinc, or other like materials.

The universal rod adapter 20 is not limited to a slap hammer/rod mechanism designed to vibrate the link and the remaining structure thereof and loosen tissue from the rod to be removed. Other vibrating/loosening devices include, but are not limited to, mechanical type vibrating devices, sonic vibrators, and other like vibrating structures.

The link 22 further includes another bore 28 which is oriented in a substantially parallel manner with respect to the threaded bore 24. The interior surface of the bore 28 is preferably smooth, however, fastening mechanisms such as threads and/or projections or other like structures are not beyond the scope of the present invention. The bore 28 substantially aligns a solid shaft 30 which includes threads 32. The solid shaft 30 is preferably a hexagonal bolt with threads 32. However, other types of solid shafts with threads are not beyond the scope of the present invention. Other types of shafts include machine screws, wood screws, and other like shafts having threads.

The link 22 further includes first means for mating or first mating structures 34, each of which is designed to mate or engage with second means for mating or second mating structures 36. The first mating means or mating structures 34 are preferably designed as recesses while the second mating means or mating structures 36 are preferably designed as projections. However, alternative combinations of mating means or mating structures are not beyond the scope of the present invention. For example, the first mating structures 34 could be designed as projections while the second mating structures 36 could be designed as recesses. As long as the first and second mating structures 34, 36 provide for a mating fit connection, such alternative embodiments are not beyond the scope of the present invention.

The first and second mating structures 34, 36 are designed to prevent rotation of means for expanding or engaging device 38, of which the second mating structures 36 are a part, relative to the link 22. The first mating structures are preferably a sector-shaped recess which corresponds to the sector-shaped projections of the second mating structure 36. However, other shapes of the respective recesses and projections are not beyond the scope of the present invention. Other shapes include, but are not limited to, elliptical, triangular, rectangular, pentagonal, octagonal, hexagonal, and other polygonal shapes.

The engaging means or engaging device 38 preferably includes a hollow shaft or sleeve 40. The hollow shaft or sleeve 40 is preferably cylindrical in shape. However, other cross-sectional shapes besides a circular shape are not beyond the scope of the present invention. Other cross-sectional shapes of the hollow shaft or sleeve 40 include, but are not limited to, elliptical, triangular, rectangular, pentagonal, octagonal, hexagonal and other polygonal shapes. The sleeve 40 is preferably shaped to correspond with the rod which is intended to be removed. Therefore, for example, if the rod being removed from the tissue of an organism is hexagonal in shape, the sleeve 40 is similarly shaped in a hexagonal manner to correspond with the inner wall of the aperture of the rod being removed.

The engaging means or engaging device 38 preferably includes frictional members 42 which are designed to engage an inner wall 18 of an aperture 19 of the rod 16 (see FIG. 5) being removed from the tissue 14 of an organism. The frictional members 42 are designed to increase the coefficient of friction between the inner wall of the rod 16 being removed and the hollow sleeve 40. The frictional members 42 are preferably threads. However, other frictional members are not beyond the scope of the present invention. Other frictional members 42 include, but are limited to, polygonal projections, sandblasted surfaces, and other like structures which increase the coefficient of friction between two surfaces.

The engaging means 38 and expanding means 48 are preferably made from metals and/or metal alloys (metal mixtures). However, other materials are not beyond the scope of the present invention. Other materials include but not limited to aluminum, carbon, cobalt, chromium, iron, nickel, tin, titanium, and zinc or other like materials. Furthermore, additional materials include ferrous alloys, non-ferrous alloys, ceramic materials, polymers, and a composite materials (any material which can engage and provide a non-slip contact with an inner wall of a rod which is desired to be removed from tissue of an organism).

The engaging means or engaging device 38 also includes openings 44 which are designed to receive projections 46 of expanding means or expanding device 48. The openings 44 are preferably U-shaped slots which correspond with the thickness of the projections 46 of the expanding device 48. The shape of the openings 44 are not limited to U-shaped slots. Other shapes include, but are not limited to, rectangular, square, and other like shapes. The openings 44 are designed to penetrate completely through the wall of the sleeve 40 so that the openings 44 basically provide for the formation of sector-shaped legs 50 which are moved outwardly by the expanding device 48. The sleeve 40 has an inner diameter $D_1$ which permits the insertion of the shaft 30 within the sleeve 40 without significant contact therebetween. However, while the preferred embodiment includes a smooth interior wall of the sleeve 40, other embodiments are not beyond the scope of the present invention where the wall includes frictional engaging members such as threads which correspond with threads 32 disposed on the shaft 30.

The sector-shaped legs 50 of the engaging means or engaging device 38 preferably include internal angled end portions 52 which are designed to have an angle which corresponds to the outer surface 54 of the expanding device 48. While the engaging means or engaging device 38 is designed to have the openings 44 to receive the projections 46 of the expanding device 48, other embodiments which have openings or slots along the outer surface 54 of the expanding device 48 are not beyond the scope of the present invention. The openings 44 are designed to prevent rotation of the expanding device 48 relative to the engaging means or engaging device 38 and link 22. As long as this relative rotation of the expanding device 48 is substantially prevented the projections and openings can be disposed on either of the engaging means or engaging device 38 and the expanding device 48.

The expanding device 48 preferably has a frustro-conical shape which is designed to engage the internal angled end portions 52. However, other shapes are not beyond the shape of the invention. Other shapes include, but are not limited to, conical, pentagonal, concentric shafts with varying diameters and other like structures which are designed to provide the relative expansion of a hollow sleeve when such a shape propagates through a central area of the sleeve. The expanding device 48 preferably includes a threaded bore 56 which is designed to receive the threads 32 of the shaft 30. While the preferred embodiment employs threads to move the expanding device 48 into the engaging means or the engaging device 38, other retraction devices are not beyond the scope of the present invention. For example, shaft 30 could be employed as the end of a hydraulic or pneumatic piston which couples with the expanding device 48 by a fastening device such as projections which engage with the shaft after insertion thereof. The hydraulic or pneumatic piston would then retract to pull the expanding device 48 into the engaging means or engaging device 38. While such an embodiment is not beyond the scope of the invention, the preferred embodiment employs screw threads in order to substantially reduce manufacturing costs and improve the overall simplicity of the invention.

The projections 46 of the expanding device 48 are preferably triangular in shape with respect to the outer surface 54 of the expanding means 48. However, other shapes are not beyond the scope of the present invention. Other shapes include, but are not limited to, rectangular, elliptical and other like shapes which prevent rotational movement of the expanding means when engaged with a corresponding slot in the engaging means 38. The projections 46 are preferably symmetrically disposed around the expanding means 48. The preferred number of projections 46 is four, but other numbers of projections are not beyond the scope of the present invention. The number of openings for slots 44 should correspond with the number of projections 46 so that a uniform expansion of the engaging means occurs to engage the frictional members 42 with a rod 16 which is being removed from the tissue 14 of an organism.

Figure 3:
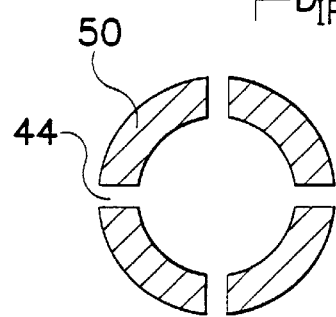
FIG. 3 is a cross-sectional view of the engaging device of the present invention.

As seen in FIG. 3, the openings or slots 44 and sector-shaped legs 50 are equal-angularly or symmetrically disposed around the circumference of the cross-section of the engaging means 38. This symmetrical distribution of the openings 44 corresponds with the symmetrical distribution of the projections 46 which provide for an even or symmetrical expansion of the engaging means when the expanding means 48 presses against the internal angled end portions.

As noted above, the cross-sectional shape and overall shape of the engaging means 38 is not limited to a circle and can include other shapes. Other shapes include, but are not limited to, elliptical, triangular, rectangular, pentagonal, octagonal, hexagonal, and other polygonal shapes.

As seen in FIG. 4, the first embodiment of the universal rod adapter 20 is shown in an assembled state. The expanding means 48 preferably includes an outer diameter $D_o$ which is less than an outer diameter $D_E$ of the engaging means 38, but which is greater than the inner diameter $D_I$ of the engaging means 38. Furthermore, the outer diameter $D_o$ of the expanding means 48 is preferably less than the diameter of the inner wall 18 of the rod 16. However, the outer diameter $D_o$ of the expanding means 48 can be greater than the outer diameter $D_E$ of the engaging means 38, but the outer diameter $D_o$ and $D_E$ of the expanding means 48 and engaging means 38 should always be less than or at least equal to the diameter $D_{IR}$ of the inner wall 18 of the rod 16 being removed from the tissue 14 of the organism so that the expanding means 48 and the engaging means 38 can slide within the inner wall 18 of the rod 16 in a substantially smooth and loose manner. At least one advantage of the present invention is that the engaging means 38 can expand to varying diameters according to the relative displacement of the expanding means 48 within the engaging means 38.

Figure 5:
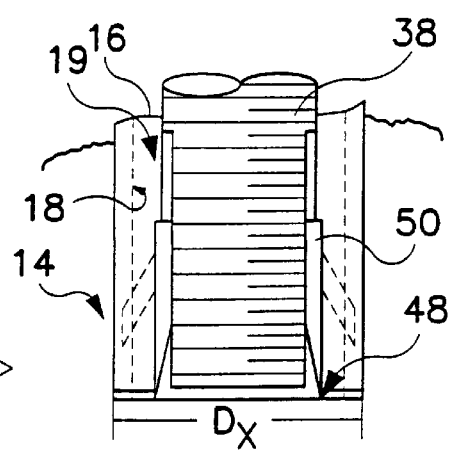
FIG. 5 is a side view of the present invention in an operational state.

As seen in FIG. 5, the inner diameter $D_I$ of the engaging means 38 near the sector-shaped legs 50 has been expanded to diameter $D_X$ due to the expanding means 48 moving into the engaging means 38 according to the rotation of the shaft 30. The frictional members 42 engage and press against the inner wall 18 of a rod 16 which is disposed in tissue 14 of an organism. The engaging means 38 facilitates the removal of the rod 16 from the tissue 14 by providing a substantially non-slip gripping mechanism in the form of a universal rod adapter 20 which attaches to the inner wall 18 of the aperture 19 of the rod 16.

As noted above, if loosening of the rod 16 becomes necessary to remove the rod 16 from the tissue 14, a slap hammer/rod mechanism 2 is employed where the rod of such a slap hammer/rod mechanism is threadably fastened to the bore 24. The slap hammer 4 of the slap hammer/rod mechanism 2 provides an impact on the planar surface 26 which in turn provides axial vibrations without providing torsion movement of the universal rod adapter 20. While torsion or rotational movement of the universal rod adapter 20 is typically not required, if such torsion or rotational movement is desired, the link 22 provides a moment arm which can rotate the engaging means 38 and expanding means 48.

However, as noted above, twisting or turning or rotational movement of the universal rod adapter may be undesirable since flesh lacerations, bone chipping, cracking or splitting of the tissue could occur during such movement since the tissue is typically very soft and/or brittle and not prone to withstand such rotational or torsional movement.

Figure 6:
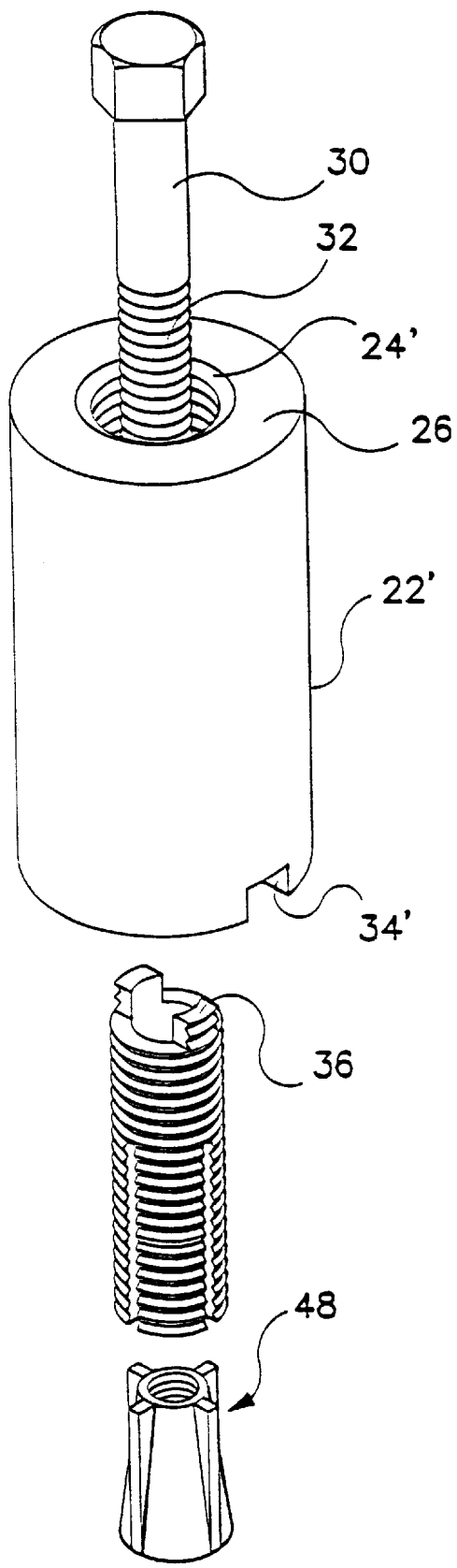
FIG. 6 is a perspective view of a second embodiment of the universal rod adapter of the present invention in a partially disassembled state.
Figure 7:
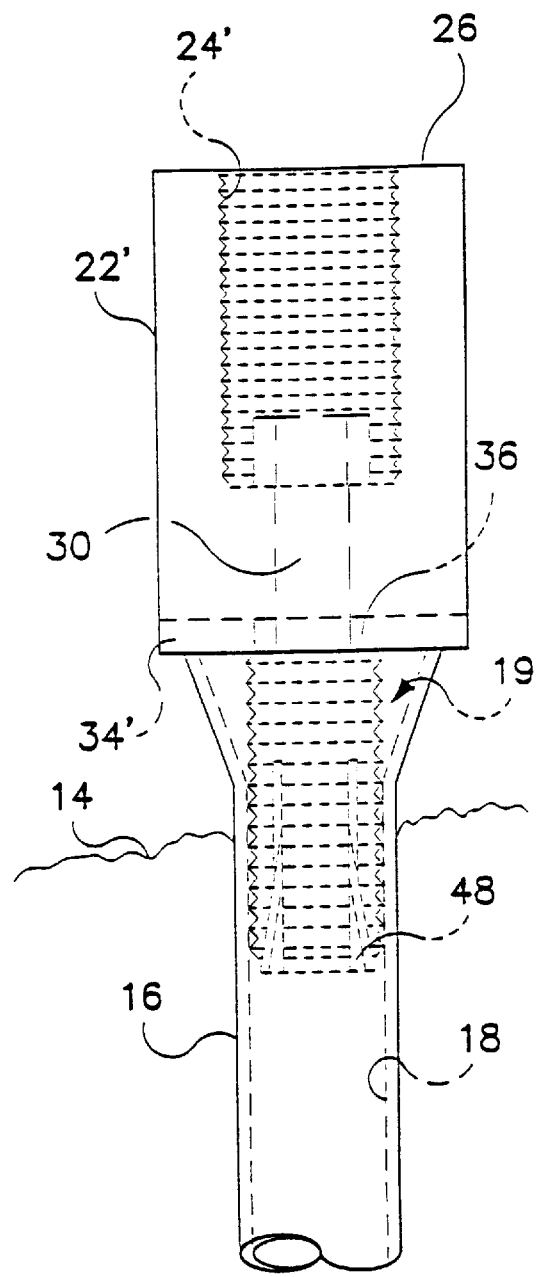
FIG. 7 is a side view of the second embodiment of the present invention with the engaging device disposed within the rod.

A second embodiment of the present invention of a universal rod adapter 20 is shown in FIGS. 6 and 7. A notable difference from the first embodiment is link 22' having a cylindrical shape in which the threaded bore 24', corresponding to the threaded bore 24 of the first embodiment, is a blind bore and of an inline nature with bore 28, rather than being off-set due to the oblong shape of link 22 shown for the first embodiment. Bore 28 is oriented in a substantially parallel manner with respect to the threaded bore 24' into which rod 6 is mated. The interior surface of the bore 28 is preferably smooth, however, fastening mechanisms such as threads and/or projections or other like structures are not beyond the scope of the present invention. (As with bore 24, bore 24' provides support for a slap hammer/rod mechanism 2 which operates in substantially similar manner as with bore 24. Likewise, with the second embodiment, as with the first embodiment, other similar types of fastening mechanisms exist for attaching to a slap hammer/rod mechanism and other vibrating/loosening devices.) The bore 28 substantially aligns a fastener 30 which includes threads 32. The solid shaft 30 is preferably a hexagonal bolt with threads 32. However, other types of solid shafts with threads are not beyond the scope of the present invention. Other types of shafts include machine screws, wood screws, and other like shafts having threads.

As elements 2, 4, 6, 26, 38, 40, 42, 44, 46, 48, 50, 52, 54 and 56 are substantively identical to those discussed with respect to the first embodiment, further explanation of such elements, or their operation, will be limited.

The link 22' further includes first means for mating or first mating structures 34', each of which is designed to mate or engage with second means for mating or second mating structures 36. The first mating means or mating structures 34' are preferably designed as recesses while the second mating means or mating structures 36 are preferably designed as projections. However, alternative combinations of mating means or mating structures are not beyond the scope of the present invention. For example, the first mating structures 34' could be designed as projections while the second mating structures 36 could be designed as recesses. As long as the first and second mating structures 34', 36 provide for a mating fit connection, such alternative embodiments are not beyond the scope of the present invention.

The first and second mating structures 34', 36 are designed to prevent rotation of means for expanding or engaging device 38, of which the second mating structures 36 are a part, relative to the link 22'. The first mating structures are preferably a sector-shaped recess which corresponds to the sector-shaped projections of the second mating structure 36. However, other shapes of the respective recesses and projections are not beyond the scope of the present invention. Other shapes include, but are not limited to, elliptical, triangular, rectangular, pentagonal, octagonal, hexagonal, and other polygonal shapes.

The present invention also provides a method for removing a rod 16 from tissue 14 of an organism comprising the steps of providing a link 22, 22' with at least one bore 28 and a first mating structure 34. An expanding device 48 with an outer angled surface 54 is then provided, where the expanding device 48 further includes an internal threaded bore 56 and projections 46 on the outer surface 54. A hollow sleeve 40 with a plurality of openings 44 and frictional members 42 disposed between the openings 44 is then provided. The hollow sleeve 40 further includes a second mating structure 36 on one end of the sleeve 40.

A fastener 30 having threads 32 is then provided. The expanding device 48 is placed in an aperture 19 of the rod 16. The sleeve 40 is placed within the aperture 19 of the rod 16. The sleeve 40 then slides over the expanding device 48. The first mating structure 34 is coupled with the second mating structure 36.

The fastener 30 is placed into the at least one bore 28 and the fastener 30 threadily engages with the expanding device 48. The fastener 30 is then rotated in a defined direction so that the expanding device 48 moves into the sleeve 40 while expanding the frictional members 42 to press against a wall 18 surrounding the aperture 19 of the rod 16. The link 22, 22' is then pulled in a direction to remove the rod 16 from the tissue 14.

The method of the present invention further includes the steps of sliding the projections 46 of the expanding device 48 into the openings 44 of the sleeve 40. The method further includes the step of providing an expanding device 48 which has a frustro-conical shape and has at least four projections 46 which are spaced around a circumference of the expanding device 48 in a substantially symmetrical manner.

The method includes a step of providing the hollow sleeve 40 with frictional members 42 that have angled end portions 52. The method further includes engaging and moving the outer surface 54 of expanding device 48 against the angled end portions 52 of the hollow sleeve 40 to provide frictional engagement between the frictional members 42 and the wall 18 surrounding/defining the aperture 19.

The present invention to provides a method and apparatus for removing a rod from tissue of an organism which can engage and remove any type of rod having a diameter and/or threading pattern which is within the range of diameters contemplated by the universal rod adapter. The present invention provides a method and apparatus which facilitates the removal of a rod from the tissue of an organism by providing a substantially non-slip gripping mechanism which attaches to a rod wall of surrounding an aperture.

With the present invention, a method and apparatus are provided for the rapid removal of a rod from tissue of an organism with out the necessity of matching serial numbers and/or part numbers of a respective rod to a respective removal tool. The present invention also provides a method and apparatus for removing a rod from the tissue of an organism which employs a universal rod extractor which can remove at least one of femoral and tibial rods.

The invention also provides a method and apparatus for removing a rod from tissue which employs a universal adapter which will fit an array of rods with wall structures of differently sized internal diameters.

The present invention provides a method and apparatus for removing a rod from tissue which substantially reduces the costs associated with the removal of rods from living tissue.

The method and apparatus for removing a rod from tissue of an organism substantially reduces the time, effort, and resources expended by the medical practitioner, especially by eliminating the task of matching rod serial number and/or part numbers with an appropriate removal tool.

The present invention for removing a rod from the tissue of an organism employs a relatively simple structure that substantially increases manufacturing efficiency thereof.

The method and apparatus for removing a rod from tissue of the present invention employs a link that forms part of a substantially non-slip gripping mechanism that attaches to a rod wall surrounding an aperture therein while providing an attachment surface for a slap hammer/rod mechanism used to vibrate the link in addition to a fastener, a hollow sleeve, and an expanding device.

The present invention facilitates axial movement of the rod while substantially reducing twisting or turning of the rod. The invention also substantially reduces potential damage to the tissue such as lacerations, bone chipping, cracking or splitting during the removal of a rod from the tissue.

The present invention provides a method and apparatus for removing a rod from tissue of an organism which employs a link which includes structures which are designed to mate with respective mating structures of an expandable engaging device. The respective mating structures of the link and the engaging device are substantially designed to prevent any rotation of the engaging device relative to the link.

With this invention, a universal rod adapter is provided which is designed to remove femoral and tibial rods, and more specifically intramedullary femoral or tibial rods.

The invention being thus described, it will be obvious that the same may be varied in many ways. Such variations are not to be regarded as a departure from the spirit and scope of the invention, and all such modifications as would be obvious to one skilled in the art were intended to be included within the scope of the following claims.

What is claimed is:

1. A universal rod adapter for removing a rod from tissue of an organism, the rod adapter comprising:

a link with at least one bore and first means for mating;

means for engaging a wall of an aperture of the rod, the aperture having a diameter, said engaging means including a hollow sleeve with a first diameter having a plurality of openings and frictional members disposed between said openings, said engaging means further including a second means for mating disposed on one end of the sleeve;

means for expanding said engaging means, said expanding means including an outer angled surface, said expanding means further including an internal threaded bore and projections on said outer angled surface;

a fastener having threads, said fastener engaging said expanding means and moving said expanding means within said engaging means, each projection of said expanding means being disposed in a respective opening of said engaging means during movement of said expanding means, said first mating means being engaged with said second mating means and substantially preventing rotational movement of said expanding means relative to said link, said expanding means changes the first diameter of said engaging means to a second diameter which is substantially greater than said first diameter and substantially equal to the diameter of the aperture in order to provide frictional engagement between said frictional members and the wall of the aperture, whereby said engaging means facilitates the removal of the rod from the tissue of the organism by providing a substantially non-slip gripping mechanism which attaches to the wall of the aperture of the rod.

2. The universal rod adapter of claim 1, wherein said at least one bore of said link includes threads.

3. The universal rod adapter of claim 2, wherein said engaging means has a substantially cylindrical shape.

4. The universal rod adapter of claim 1 wherein said expanding means has a substantially conical shape.

5. The universal rod adapter of claim 4, wherein said expanding means has a substantially frustro-conical shape.

6. The universal rod adapter of claim 5, wherein said expanding means includes at least four projections which have a substantially triangular shape relative to the outer surface of the expanding means, said engaging means including at least four openings.

7. The universal rod adapter of claim 6, wherein said at least four projections are spaced around a circumference of the expanding means in a substantially symmetrical manner, said at least four openings are spaced around a circumference of the engaging means in a substantially symmetrical manner.

8. The universal rod adapter of claim 4, wherein said frictional members include internal angled end portions having a substantially sector cross sectional shape which engage with said outer angled surface of said expanding means during expansion of said engaging means.

9. The universal rod adapter of claims 8, wherein said frictional members include at least one of threads and serrations on an external surface thereof.

10. The universal rod adapter of claim 2, wherein said first mating means includes a plurality of recesses spaced around said at least one bore in a substantially symmetrical manner.

11. The universal rod adapter of claim 7, wherein said second mating means includes a plurality of projections spaced around an end of said engaging means in a substantially symmetrical manner.

12. The universal rod adapter of claim 1, wherein the link has one bore, said one bore being a stepped bore.

13. A method for removing a rod from tissue of an organism comprising the steps of:
providing a link with at least one bore with a first mating structure;
providing an expanding device with an outer angled surface, the expanding device further including an internal threaded bore and projections on the outer surface;
providing a hollow sleeve with a plurality of openings and frictional members disposed between the openings, the hollow sleeve further including a second mating structure on one end of the sleeve;
providing a fastener having threads;
placing the expanding device in an aperture of the rod;
placing the sleeve within the aperture of the rod;
sliding the sleeve over the expanding device; coupling the first mating structure with the second mating structure;
placing the threaded fastener into the at least one bore;
threadily engaging the fastener with the expanding device;
rotating the fastener in a defined direction so that the expanding device moves into the sleeve while expanding the frictional members to press against a wall of the aperture of the rod; and
pulling the link in a direction to remove the rod from the tissue.

14. The method of claim 13, further comprising the step of sliding the projections of the expanding device into the openings of the sleeve.

15. The method of claim 14, wherein the step of providing the expanding device further includes the step of providing an expanding device which has a frustro-conical shape.

16. The method of claim 15, wherein the step of providing the expanding device further includes the step of providing an expanding device with at least four projections.

17. The method of claim 16, wherein the step of providing the at least four projections, includes spacing the four projections around a circumference of the expanding device in a substantially symmetrical manner.

18. The method of claim 15, wherein the step of providing the hollow sleeve includes the step of providing a hollow sleeve with frictional members that have angled end portions, the method further comprising the step of engaging and moving the outer surface of the expanding device against the angled end portions of the hollow sleeve.

19. The method of claim 13, wherein the step of providing the link with the first mating structure includes providing a link with a first mating structure having a plurality of recesses.

20. The method of claim 19, wherein the step of providing the hollow sleeve with the second mating structure includes providing a hollow sleeve with a second mating structure having a plurality of projections.

21. The method of claim 20, wherein the step of coupling the first mating structure with the second mating structure includes mating each projection of the sleeve with a respective recess of the link.

22. The method of claim 18, wherein the step of providing the hollow sleeve further includes providing a hollow sleeve with frictional members that include at least one of threads and serrations on an external surface thereof.

23. The method of claim 13, wherein the step of providing a link with at least one bore with a first mating structure, includes providing a link with one bore, said one bore being a stepped bore.

* * * * *